United States Patent
Cheng et al.

(10) Patent No.: US 10,338,006 B2
(45) Date of Patent: Jul. 2, 2019

(54) METHOD AND APPARATUS FOR ALIGNING AND INSPECTING ELECTRONIC COMPONENTS

(71) Applicant: ASM Technology Singapore Pte Ltd, Singapore (SG)

(72) Inventors: Chi Wah Cheng, Hong Kong (HK); Kai Fung Lau, Hong Kong (HK); Hoi Shuen Tang, Hong Kong (HK)

(73) Assignee: ASM TECHNOLOGY SINGAPORE PTE LTD, Singapore (SG)

( * ) Notice: Subject to any disclaimer, the term of this patent is extended or adjusted under 35 U.S.C. 154(b) by 103 days.

(21) Appl. No.: 15/623,458

(22) Filed: Jun. 15, 2017

(65) Prior Publication Data

US 2018/0364180 A1 Dec. 20, 2018

(51) Int. Cl.
*G06T 7/00* (2017.01)
*G06T 7/70* (2017.01)
*G01N 21/01* (2006.01)
*G01N 21/95* (2006.01)

(52) U.S. Cl.
CPC ......... *G01N 21/9503* (2013.01); *G01N 21/01* (2013.01); *G06T 7/0004* (2013.01); *G06T 7/70* (2017.01); *G01N 2201/0415* (2013.01); *G06T 2207/30148* (2013.01)

(58) Field of Classification Search
CPC .............. G06T 7/0004; G06T 7/13; G06T 2207/30148; G06T 2219/2004
See application file for complete search history.

(56) References Cited

U.S. PATENT DOCUMENTS

| | | | |
|---|---|---|---|
| 2015/0204943 A1* | 7/2015 | Yip | G01R 31/2891 324/750.22 |
| 2015/0370244 A1* | 12/2015 | Siu | G05B 19/4182 700/114 |
| 2016/0081198 A1* | 3/2016 | Cheung | H05K 3/32 29/593 |
| 2017/0062256 A1* | 3/2017 | Cheung | H01L 21/681 |
| 2017/0116720 A1* | 4/2017 | Hofmann | G06T 7/001 |
| 2018/0252766 A1* | 9/2018 | Cheng | G01B 11/26 |

\* cited by examiner

*Primary Examiner* — Shawn Decenzo
(74) *Attorney, Agent, or Firm* — Ostrolenk Faber LLP

(57) ABSTRACT

A method for automated alignment of electronic components with respect to one or more inspection devices for inspecting the electronic components, each electronic component having a plurality of side surfaces. The method comprises: positioning each electronic component relative to an imaging device; determining, by the imaging device, an angular offset and a linear offset between each side surface of the electronic component and the one or more inspection devices; positioning each electronic component relative to the inspection devices; effecting alignment between each side surface and the one or more inspection devices in accordance with the respective angular and linear offsets; and inspecting each side surface after effecting alignment between the side surface and the inspection devices.

18 Claims, 10 Drawing Sheets

METHOD AND APPARATUS FOR ALIGNING AND INSPECTING ELECTRONIC COMPONENTS

TECHNICAL FIELD

The present disclosure generally relates to a method and apparatus for aligning and inspecting electronic components. More particularly, the present disclosure describes various embodiments of a method for automated alignment of the electronic components with respect to one or more inspection devices for inspecting the electronic components, as well as an apparatus for automated alignment and inspection of the electronic components.

BACKGROUND

Electronic components or devices are extracted from wafers or substrates of semiconductor material for semiconductor assembly and packaging subsequently. The electronic components in the wafers which may not have moulding compound encapsulation protection are subjected to potential defects, such as cracks and chipping, during dicing processes wherein the electronic components are separated or singulated from the wafers. Presence of such cracks or chipping defects in a separated electronic component are likely to propagate around the electronic component. Due to stresses induced by environmental thermal cycling, the defects may eventually cause premature failure of the final semiconductor product assembled with the electronic component, thereby leading to quality issues of the final semiconductor product.

Manufacturers of semiconductor products or chips rely on automated optical inspection machines to inspect the defects on top and bottom surfaces of the separated electronic component. However, with reference to FIG. 1, if the electronic component 10 has crack defects 12 initiated on one or more of the side surfaces 14 of the electronic component but have not yet propagated to the top surface 16 or the bottom surface 18, the top and bottom surfaces 16, 18 would be absent of defects. The inspection machine inspecting only the top surface 16 and/or the bottom surface 18 would incorrectly pass the electronic component 10 as being free of defects. As such, defective electronic components 10 with defects on the side surfaces 14 but not on the top surface 16 or the bottom surface 18 cannot be screened out from non-defective electronic components 10.

One existing solution to this problem is the use of an inspection station in association with a turret-type die sorting machine to inspect defects present at four side surfaces 14 of electronic components 10. With reference to FIG. 2, there is shown such a turret-type die sorting machine 100 having a turret 102 and a plurality of pick heads 104 arranged circumferentially around the turret 102. The machine 100 includes an inspection station 106 for inspecting the electronic components 10 after the pick heads 104 pick and transfer the electronic components 10 to the inspection station 106. The inspection station 106 has four mirrors 108 that make use of inspection optics to inspect the four side surfaces 14 of each electronic component 10. Specifically, each mirror 108 is paired with a side surface 14 such that the four mirrors 108 capture images of the four side surfaces 14 to a camera inside the inspection station 106.

Typically, the electronic components 10 are fed to the machine 100 by using a feeding mechanism, such as a wafer table, a detaper feeder, a tray loader, a bowl feeder or a conveyor. The electronic components 10 are then separated and picked individually by the pick heads 104 to be transferred by the turret 102 to the inspection station 106. No matter which feeding mechanism is utilized, each electronic component 10 may have a different angular and translational positional offset with respect to the center of a pick head 104 after the electronic component 10 has been transferred to the pick head 104, due to an offset introduced during the die pick up process. To increase processing speed, the electronic components 10 are fed in bulk and they may be in various orientations when they are fed to the pick heads 104. Thus, both the positions and the orientations of these electronic components 10 will not be consistent with respect to the turret 102 when they are picked up and transferred to the inspection station 106, resulting in misalignment between the electronic components 10 and the inspection station 106.

As shown in FIG. 2, the machine 100 includes a precising station 110 to align the electronic components 10 with respect to the inspection station 106. The precising station 110 is positioned before the inspection station 106 such that an electronic component 10 held by a pick head 104 is first aligned to a position with respect to the focal distance and angle of the four mirrors 108 in the inspection station 106, so as to ensure the captured images of the side surfaces 14 are well-focused. Referring to FIG. 3A, the precising station 110 has motorized clamps 112 to mechanically align the electronic component 10 in terms of position and angular orientation with respect to the mirrors 108 in the inspection station 106 after the precising station 110. FIG. 3B illustrates the electronic component 10 with the side surfaces 14 being aligned with respect to the mirrors 108.

If the precising station 110 does not align the electronic component 10 before transferring to the inspection station 106, the side surfaces 14 will not be aligned in the correct focal distance and angle with respect to the mirrors 108, as shown in FIG. 4A. The misalignment will result in images that are out of focus and blur. On the other hand, if the precising station 110 aligns the electronic component 10 first, the side surfaces 14 can be aligned appropriately, as shown in FIG. 4B. The alignment will result in images that are focused and clear.

However, the machine 100 has a disadvantage when high optical resolution microscopic grade optics are used for detecting very small chipping and fine crack defects. This is because the depth of field of microscopic grade optics is limited to around ±15 µm for an optical resolution of approximately 2 µm. This means that the precising station 110 has to achieve a very high standard of precision when aligning the electronic component 10 in order to ensure that the side surfaces 14 can be accurately aligned in terms of position and angular orientation with respect to the mirrors 108 of the subsequent inspection station 106.

To achieve this standard of precision, the clamps 112 have a very low tolerance such that they can clamp the electronic component 10 tightly with very limited, or no clearance. However, this tight clamping of electronic components 10 is undesirable for wafers without protection from molding compound encapsulation as the bare die is prone to defects such as cracks or chipping caused by the mechanical clamping action. Another problem is that due to the low tolerance of the clamps 112, they cannot handle electronic components 10 with variations in sizes and dimensions. FIG. 5 illustrates the inspection station 106 inspecting an electronic component 10 with a different size which may be caused by cutting offsets arising from variation of dicing blade thickness. This size difference results in one of the side surfaces 14 (affected side surface 14') being at a different distance from the corresponding mirror 108' as compared to the distances between the other side surfaces 14 and their respective corresponding mirrors 108. As such, the focal distance between the affected side surface 14' and the corresponding mirror 108' is not ideal and the image of the affected side surface 14' will be out of focus and blur. The image cannot be used to determine the presence of small chipping or fine crack defects on the affected side surface 14'.

Therefore, in order to address or alleviate at least one of the aforementioned problems and/or disadvantages, there is a need to provide a method and apparatus for aligning and inspecting electronic components, in which there is at least one improvement and/or advantage over the aforementioned prior art.

SUMMARY

According to a first aspect of the present disclosure, there is a method for automated alignment of electronic components with respect to one or more inspection devices for inspecting the electronic components, each electronic component having a plurality of side surfaces. The method comprises: positioning each electronic component relative to an imaging device; determining, by the imaging device, an angular offset and a linear offset between each side surface of the electronic component and the one or more inspection devices; positioning each electronic component relative to the inspection devices; effecting alignment between each side surface and the one or more inspection devices in accordance with the respective angular and linear offsets; and inspecting each side surface after effecting alignment between the side surface and the inspection devices.

According to a second aspect of the present disclosure, there is an automated alignment and inspection of electronic components, each electronic component having a plurality of side surfaces. The apparatus comprises: a rotary device for positioning the electronic components; a plurality of pick heads arranged circumferentially around the rotary device, each pick head being configured for holding an electronic component; one or more inspection devices configured for inspecting the side surfaces of the electronic components; an imaging device for determining an angular offset and a linear offset between each side surface and the inspection devices; and one or more adjustment devices for effecting alignment between each side surface and the inspection devices in accordance with the respective angular and linear offsets, wherein the one or more inspection devices is operative to inspect each side surface after the one or more adjustment devices effect alignment between the side surface and the one or more inspection devices.

An advantage of the present disclosure is that electronic components in misaligned orientations can be aligned with respect to inspection devices after determining the angular and linear offsets. As the electronic components may have inconsistent die sizes and cut angles caused by improper dicing processes, alignment of the electronic components could not be achieved by conventional precising clamps. The arrangement of the clamps is precisely defined with low tolerances, and electronic components with inconsistent sizes/angles cannot be aligned by such clamps. According to the present disclosure, electronic components with inconsistent sizes/angles can be aligned, thereby allowing the inspection devices to precisely focus on the side surfaces to capture focused and clear images of the side surfaces for detection of defects.

A method and apparatus for aligning and inspecting electronic components according to the present disclosure are thus disclosed herein. Various features, aspects, and advantages of the present disclosure will become more apparent from the following detailed description of the embodiments of the present disclosure, by way of non-limiting examples only, along with the accompanying drawings in accordance with embodiments of the present disclosure.

DETAILED DESCRIPTION

For purposes of brevity and clarity, descriptions of embodiments of the present disclosure are directed to a method and apparatus for aligning and inspecting electronic components in accordance with the drawings. While aspects of the present disclosure will be described in conjunction with the embodiments provided herein, it will be understood that they are not intended to limit the present disclosure to these embodiments.

Figure 1:
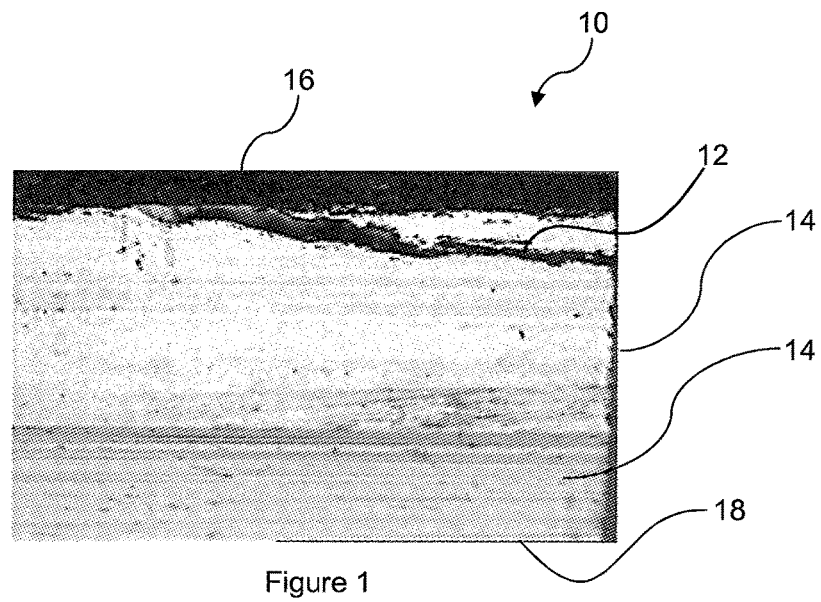
FIG. 1 illustrates a side surface of a defective electronic component.
Figure 2:
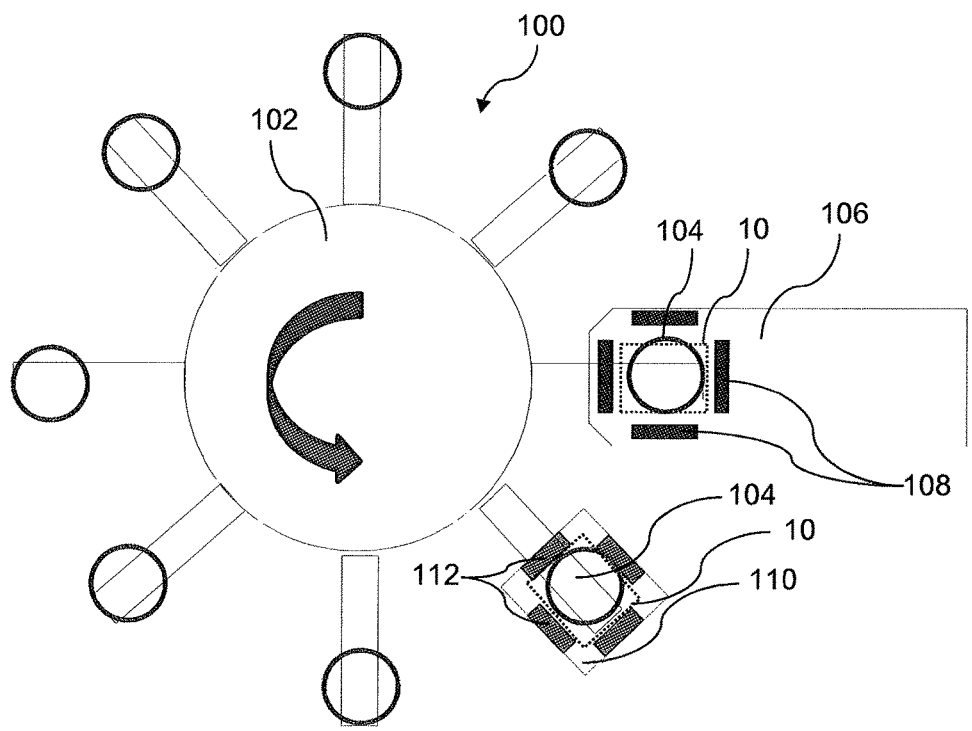
FIG. 2 illustrates a turret-type die sorting machine.
Figure 3A:
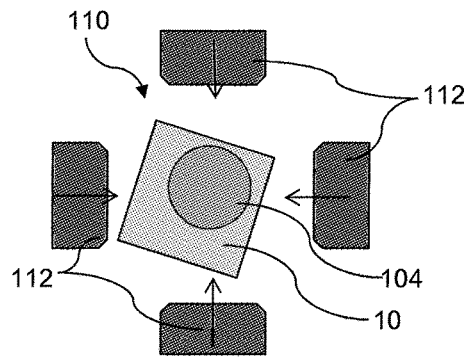
FIGS. 3A and 3B illustrate different views of a precising station of the turret-type die sorting machine.
Figure 3B:
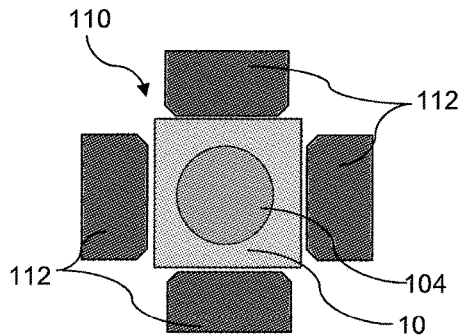
Figure 4A:
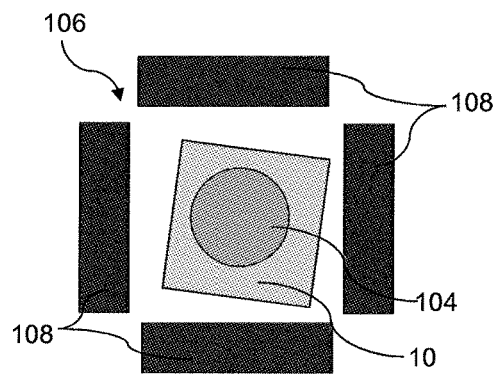
FIGS. 4A and 4B illustrate different views of an inspection station of the turret-type die sorting machine.
Figure 4B:
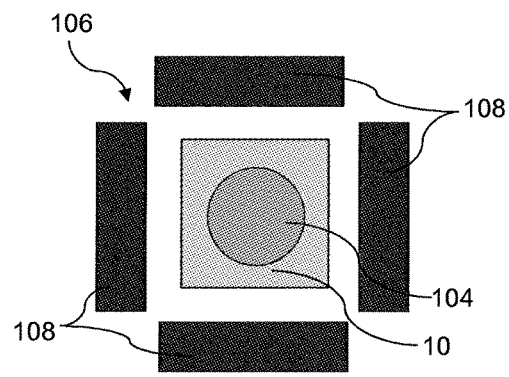
Figure 5:
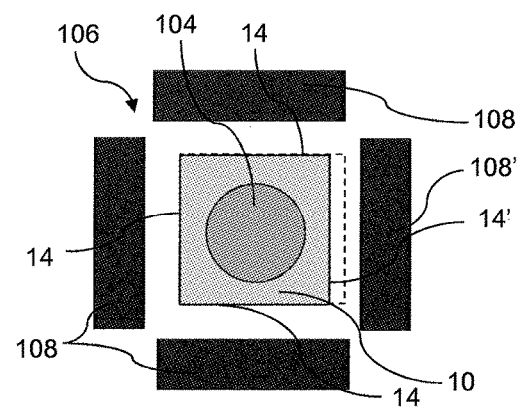
FIG. 5 illustrates the inspection station inspecting an electronic component with a different size.
Figure 6:
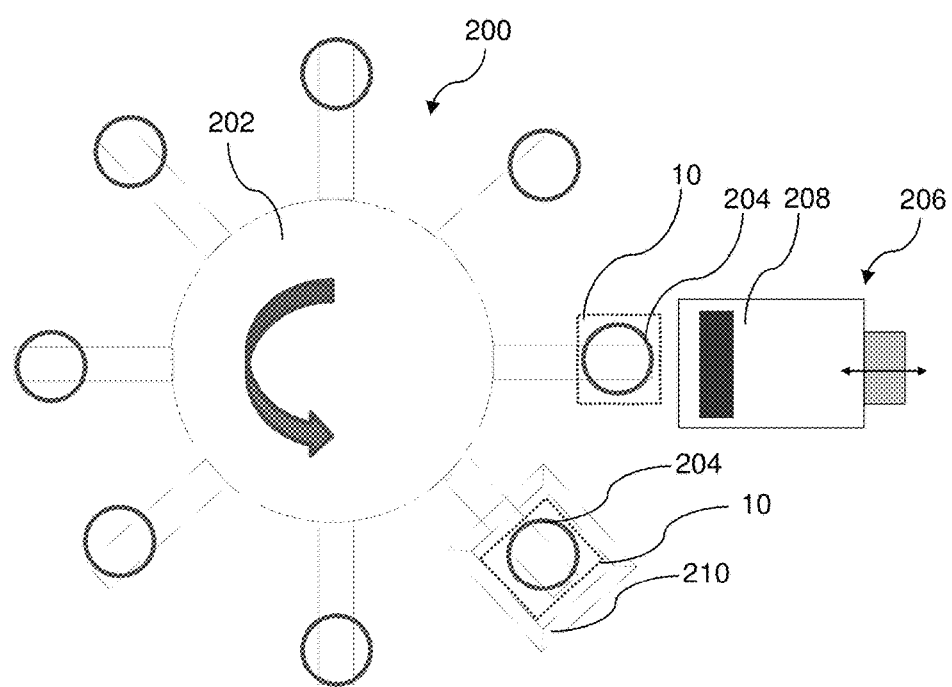
FIG. 6 illustrates an apparatus for aligning and inspecting electronic components, in accordance with a first embodiment of the present disclosure.

In a first embodiment of the present disclosure with reference to FIG. 6, there is an apparatus 200 configured for aligning and inspecting electronic components 10 such as semiconductor die, components or packages, each electronic component 10 having a plurality of side surfaces 14. The apparatus 200 includes a rotary device in the form of a turret 202 for transferring the electronic components 10 in a rotational motion. The turret 202 includes a plurality of pick heads 204 coupled to and arranged circumferentially around the turret 202. The pick heads 204 are arranged such that the centre of each pick head 204 is positioned along a circumferential travel path of the turret 202, and such that the pick heads 204 are separated by equal distances. This separation may also be referred to as an indexing pitch of the turret 202.

The electronic components 10 are fed to the pick heads 204 by a feeding station which may be a wafer table, a detaper feeder, a tray loader, a bowl feeder, or a conveyor for transferring the electronic components 10 to the pick heads 204. Each pick head 204 is configured for holding an electronic component 10 for transfer by the turret 202. The pick heads 204 may operate by way of vacuum suction generated at orifices of the pick heads 204 for picking up the electronic components 10. The turret 202 rotates in an anti-clockwise direction (as viewed from the top) to transfer or deliver the electronic components 10 to other stations located further downstream.

The apparatus 200 includes an inspection station 206 having an inspection device 208 for inspecting the electronic components 10. The inspection device 208 may include a mirror for directing light from the electronic components 10 to an image capture device or camera in the inspection station 206 for capturing images of the electronic components 10.

The apparatus 200 further includes an imaging device 210, such as an up-look camera. The imaging device 210 is positioned adjacent to the turret 202 such that an optical centre of the imaging device 210 is positioned along the circumferential travel path of the turret 202. More specifically, the imaging device 210 may be positioned one indexing pitch before or upstream of the inspection station 206 and in a fixed position with respect to the inspection station 206.

During operation of the apparatus 200, electronic components 10 are fed to the turret 202. A pick head 204 that has picked up an electronic component 10 will be conveyed by the turret 202 to the imaging device 210 and the inspection station 206. However, due to angular and/or translational offsets introduced during the die pick up process, the electronic component 10 may not be aligned with the inspection device 208. The imaging device 210 is configured for determining the orientation of the electronic component 10 and its degree of misalignment with respect to the inspection device 208. As the imaging device 210 is positioned before the inspection station 206, any misalignment can be determined before the electronic component 10 is transferred downstream to the inspection station 206.

Figure 7:
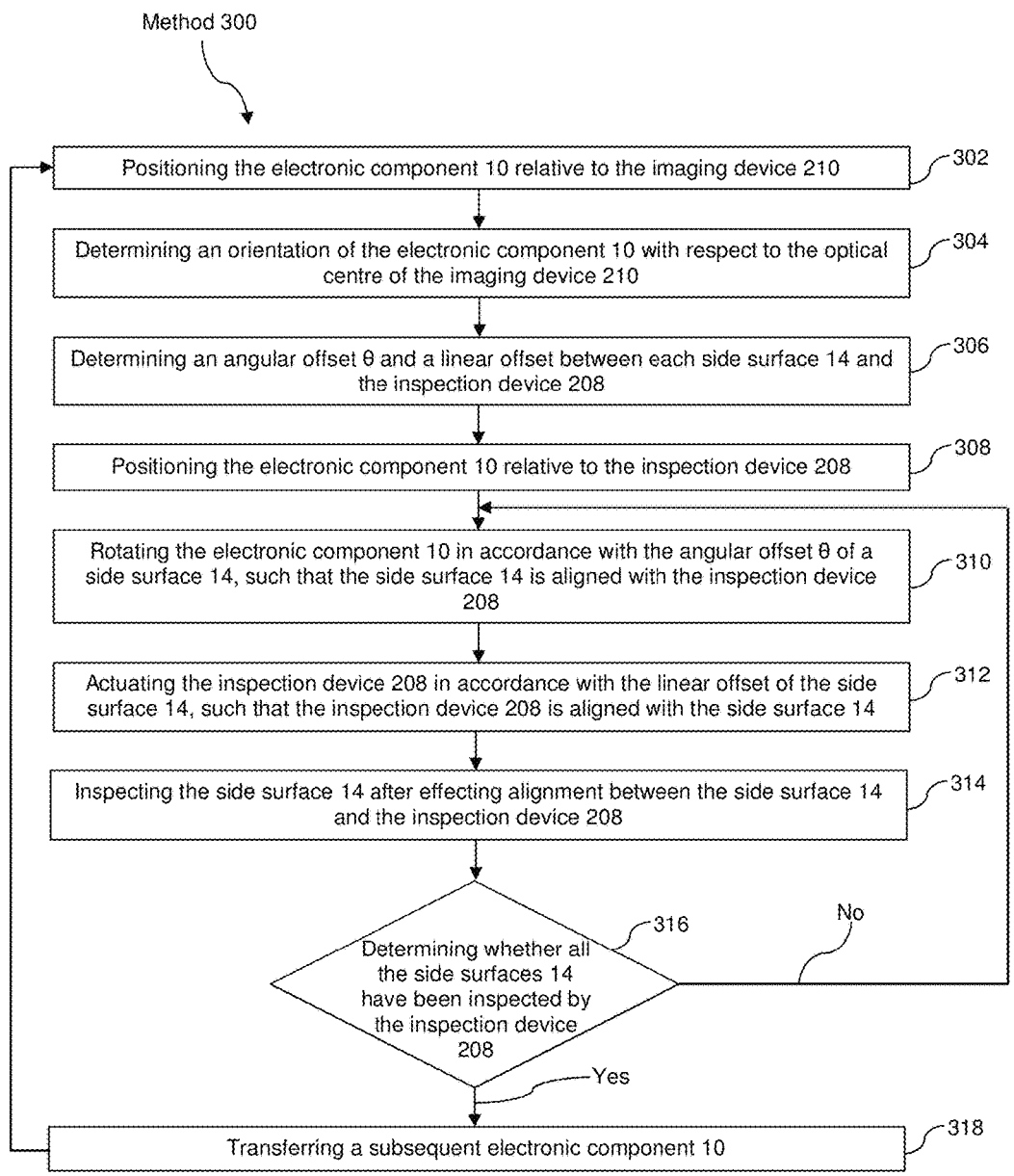
FIG. 7 illustrates a flowchart of a method for aligning and inspecting electronic components, in accordance with the first embodiment of the present disclosure.

In the first embodiment of the present disclosure and with reference to FIG. 7, there is a method 300 for automated alignment of electronic components 10 with respect to an inspection device 208 for inspecting the electronic components 10. Each electronic component 10 has a plurality of side surfaces 14, such as four side surfaces 14 in a quadrilateral arrangement. The method 300 may be performed by a computing system, processor, or controller of the apparatus 200 that is communicatively linked with various stations of the apparatus 200, such as by wired connections and/or wireless communications protocols.

The electronic components 10 are fed to the apparatus 200 sequentially/individually and each electronic component 10 is picked up by a pick head 204. The method 300 includes a step 302 of positioning the electronic component 10 relative to the imaging device 210. Specifically, the turret 202 conveys the electronic component 10 to be positioned above or indexed to the imaging device 210, such that the electronic component 10 is within a field of view of the imaging device 210.

Figure 8:
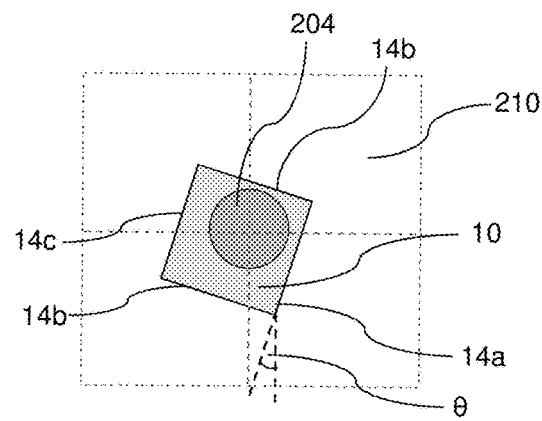
FIG. 8 illustrates an orientation of an electronic component determined by an imaging device of the apparatus.

The method 300 includes a step 304 of determining, by the imaging device 210, an orientation of the electronic component 10 with respect to the optical centre of the imaging device 210. An example is shown in FIG. 8 wherein the electronic component 10 has four side surfaces 14a,b,c,d in a rectangular arrangement. As the imaging device 210 is in a fixed position with respect to the inspection station 206, the position of the inspection device 208 is known with respect to the optical centre of the imaging device 210 and the circumferential travel path. In a subsequent step 306, the imaging device 210 determines an angular offset θ and a linear offset between each side surface 14a/b/c/d and the inspection device 208.

The method 300 includes a step 308 of positioning the electronic component 10 relative to the inspection device 208. Specifically, the turret 202 conveys the electronic component 10 to be positioned adjacent to the inspection device 208. It will be appreciated that it is not necessary for the electronic component 10 to be precisely adjacent and aligned to the inspection device 208, as any misalignment can be adjusted by the method 300 as described herein.

Figure 9A:
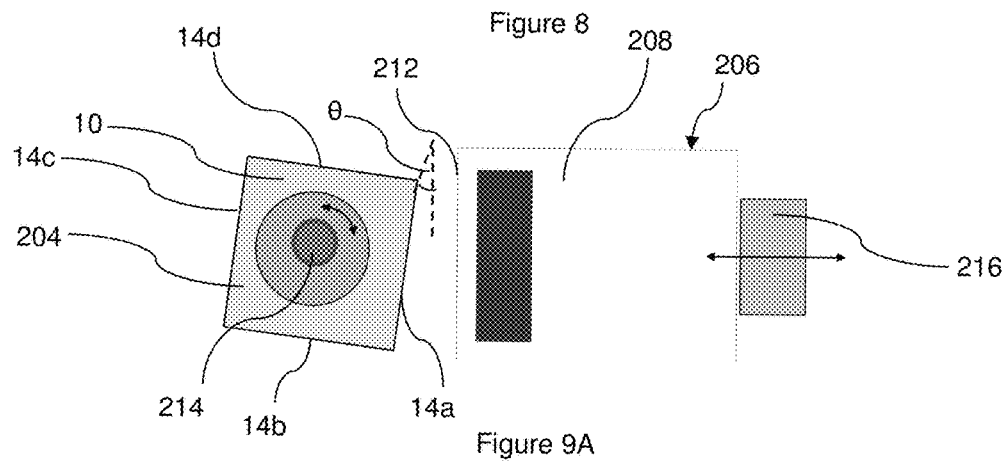
FIGS. 9A and 9B illustrate alignment of a side surface of the electronic component with respect to an inspection device of the apparatus.
Figure 9B:
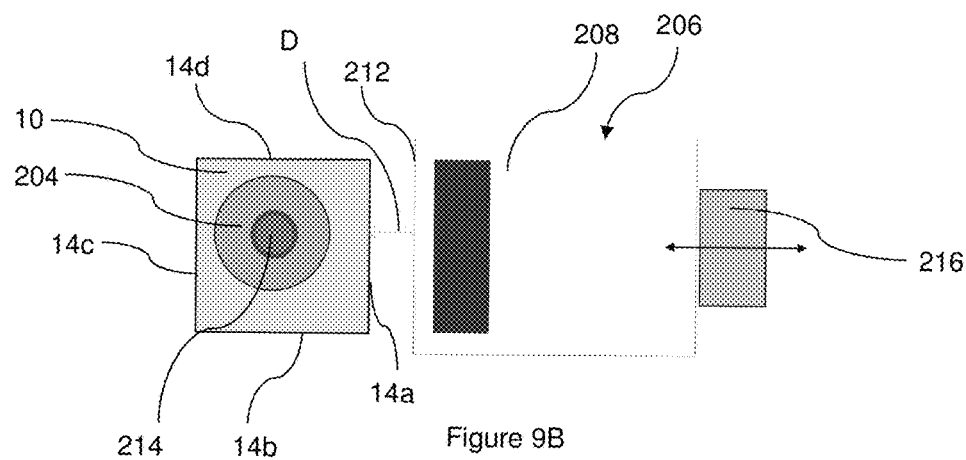

Referring to FIG. 9A, the electronic component 10 is positioned adjacent to the inspection device 208 in a misaligned orientation. For example, the first side surface 14a is misaligned and not parallel to an opposing surface 212 of the inspection device 208; the first side surface 14a has an angular offset θ with respect to the opposing surface 212. Referring to FIG. 9B, even if the first side surface 14a is aligned and parallel to the opposing surface 212, or any angular offset θ has been corrected, there is a distance D between the first side surface 14a and the opposing surface 212. The distance D may not be ideal for the inspection device 208 to accurately inspect the first side surface 14a for defects, such as by capturing a focused and clear image of the first side surface 14a. There may be a linear offset between the first side surface 14a and the opposing surface 212, wherein this linear offset refers to the difference between the distance D and the ideal focal distance of the inspection device 208.

Figure 10:
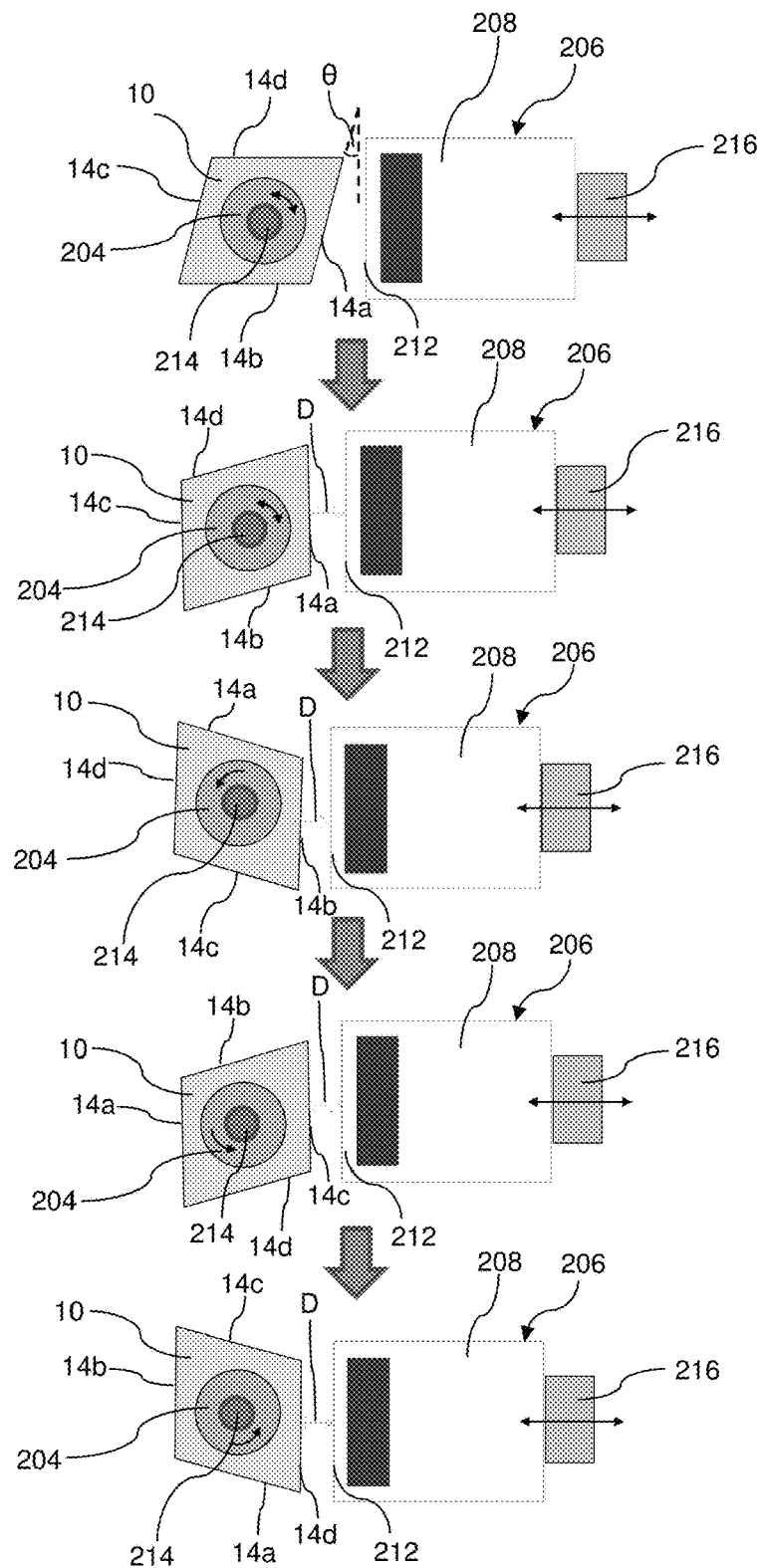
FIG. 10 illustrates alignment of the side surfaces of the electronic component with respect to the inspection device.

With reference to FIG. 10, in the step 308, an electronic component 10 is positioned adjacent to the inspection device 208. This electronic component 10 has four side surfaces 14a,b,c,d in a parallelogram arrangement. Each of the side surfaces 14a/b/c/d has an angular offset θ and a linear offset with respect to the inspection device 208, specifically with the opposing surface 212 thereof. The apparatus 200 includes one or more adjustment devices for effecting alignment between each side surface 14a/b/c/d and the inspection device 208 in accordance with the respective angular offsets θ and linear offsets. In one variation of the adjustment devices, the adjustment devices include an angular adjustment device, such as a rotary motor 214 coupled to the pick head 204, and a linear adjustment device, such as a linear actuator 216 coupled to the inspection device 208.

The method 300 includes a step 310 of rotating, by the rotary motor 214, the electronic component 10 held at the pick head 204 in accordance with the angular offset θ of a side surface 14 such as the first side surface 14a, such that the first side surface 14a is aligned with the inspection device 208. The method 300 includes a step 312 of actuating, by the linear actuator 216, the inspection device 208 in accordance with the linear offset of the first side surface 14a, such that the inspection device 208 is focused on the first side surface 14a. Thus, in the steps 310 and 312, the adjustment devices adjust the electronic component 10 or inspection device 208 to effect alignment between the first side surface 14a and the inspection device 208. At this alignment, the first side surface 14a is parallel to the opposing surface 212 of the inspection device 208 and the distance D therebetween is the required focal distance of the inspection device 208. The steps 310 and/or 312 may be performed after the electronic component 10 is positioned adjacent to the inspection device 208. Alternatively, the steps 310 and/or 312 may be performed while the component 10 is are being transferred by the turret 202 to the inspection device 208.

The method includes a step 314 of inspecting the first side surface 14a after effecting alignment between the first side surface 14a and the inspection device 208. The inspection of the first side surface 14a may include capturing an image thereof by the inspection device 208 for assessing the presence of defects thereon.

The method 300 includes a step 316 of determining whether all the side surfaces 14 have been inspected by the inspection device 208. If not, the step 316 returns to the step 310. In this subsequent iteration of the step 310, the rotary motor 214 rotates the electronic component 10 such that a subsequent side surface such as the second side surface 14b is aligned with the inspection device 208. As the angle between the second side surface 14b and the first side surface 14a, as well as the angular offset θ of the first side surface 14a, is known from the step 304, the angular offset θ of the second side surface 14b can be determined in the step 304. In this iteration of the step 310, the electronic component 10 is rotated in accordance with the angular offset θ of the second side surface 14b.

Similarly, in the subsequent iteration of the step 312, the linear actuator 216 rotates the electronic component 10 such that the inspection device 208 is focused on the subsequent side surface (second side surface 14b). Accordingly, the second side surface 14b is aligned with the inspection device 208. At this alignment, the second side surface 14b is parallel to the opposing surface 212 of the inspection device 208 and the distance D therebetween is the ideal focal distance of the inspection device 208. The subsequent iteration of the step 314 inspects the second side surface 14b after effecting alignment between the second side surface 14b and the inspection device 208.

It will be appreciated that the steps 310, 312, and 314 are repeated for the remaining side surfaces 14 of the electronic component 10, namely the third side surface 14c and fourth side surface 14d in this example. Accordingly, the inspection device 208 is configured for sequentially inspecting the side surfaces 14 of the electronic component 10. After the step 316 has determined that all the side surfaces 14 have been inspected by the inspection device 208, the step 316 proceeds to a step 318 of transferring a subsequent electronic component 10. The steps of the method 300 are repeated for a subsequent electronic component 10. The electronic component 10 which has been inspected may be transferred to a subsequent station for further processing. This frees up the inspection device 208 to receive the subsequent electronic component 10 for inspection thereof.

Figure 11A:
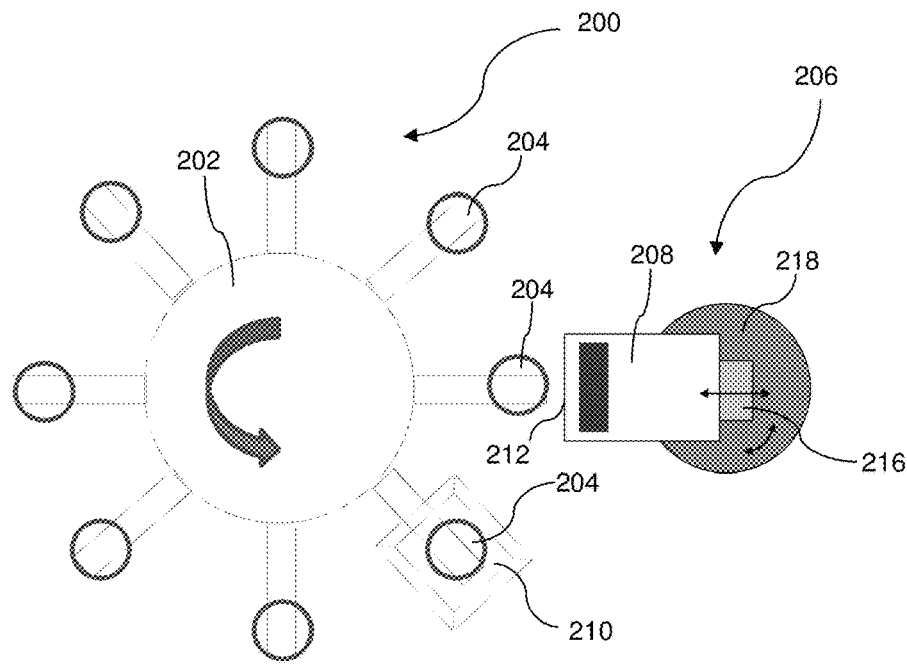
FIGS. 11A and 11B illustrate adjustment devices of the apparatus for effecting alignment, in accordance with one embodiment of the present disclosure.
Figure 11B:
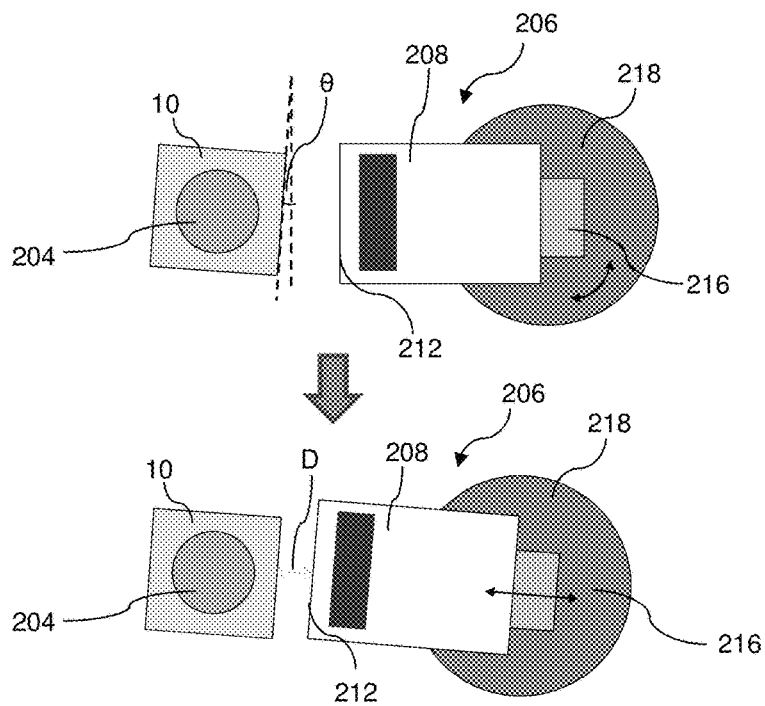

Referring to FIGS. 11A and 11B, in another variation of the adjustment devices, the adjustment devices include the linear adjustment device or linear actuator 216 coupled to the inspection device 208. Furthermore, the adjustment devices include an angular adjustment device such as a rotary motor 218 coupled to the inspection device 208. The rotary motor 218 is configured for rotating the inspection device 208 in accordance with the respective angular offsets 8 to align the inspection device 208, specifically the opposing surface 212 thereof, with the side surfaces 14 of each electronic component 10. In yet another variation, the adjustment devices include the linear actuator 216 and rotary motor coupled to the inspection device 208, as well as the rotary motor 214 coupled to the pick head 204. The rotary motors 214 and 218 may cooperate to rotate the electronic component 10 and/or inspection device 208 and correct the respective angular offsets 8, thereby effecting alignment between each side surface 14 and the opposing surface 212. It will be appreciated that linear actuators may be coupled to each pick head 204 for correcting the respective linear offsets, possibly in cooperation with the linear actuator 216 coupled to the inspection device 208.

Figure 12:
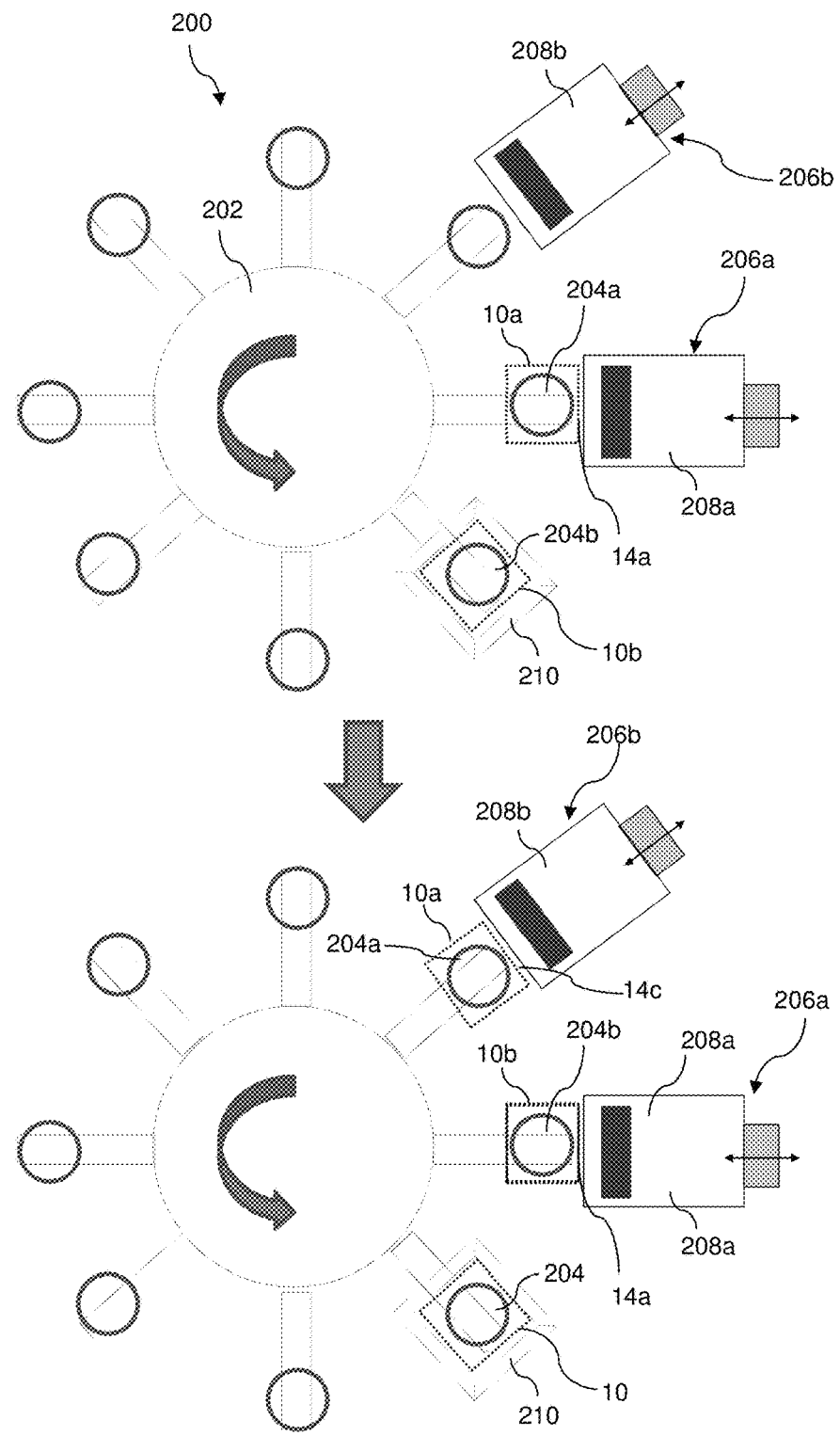
FIG. 12 illustrates an apparatus for aligning and inspecting electronic components, in accordance with a second embodiment of the present disclosure.

In a second embodiment of the present disclosure, there is another variation of the apparatus 200 as shown in FIG. 12. Similar to the first embodiment, the apparatus 200 includes a turret 202 for positioning the electronic components 10, a plurality of pick heads 204 for holding the electronic components 10, and an imaging device 210 for determining the angular and linear offsets. However, the apparatus 200 includes a first inspection station 206a and a second inspection station 206b, which may be positioned one indexing pitch apart from each other. The imaging device 210 may also be positioned one indexing pitch before or upstream of the first inspection station 206a and in a fixed position with respect to the inspection stations 206a,b. Each inspection station 206a/b has an inspection device 208a/b respectively, and each inspection device 208a/b is positioned along a circumferential travel path that is concentric to the circumferential travel path of the turret 202.

The inspection devices 208a,b are arranged such that each inspection device 208a/b is configured to view an electronic component 10 and both electronic components 10 can be aligned and inspected simultaneously. It will be appreciated that while the turret 202 conveys a first pick head 204a to transfer a first electronic component 10a to the imaging device 210, a second pick head 204b picks up a second electronic component 10b. For example, when the first electronic component 10a is indexed to the imaging device 210, the second electronic component 10b located one indexing pitch behind is picked up by the second pick head 204b.

Figure 13:
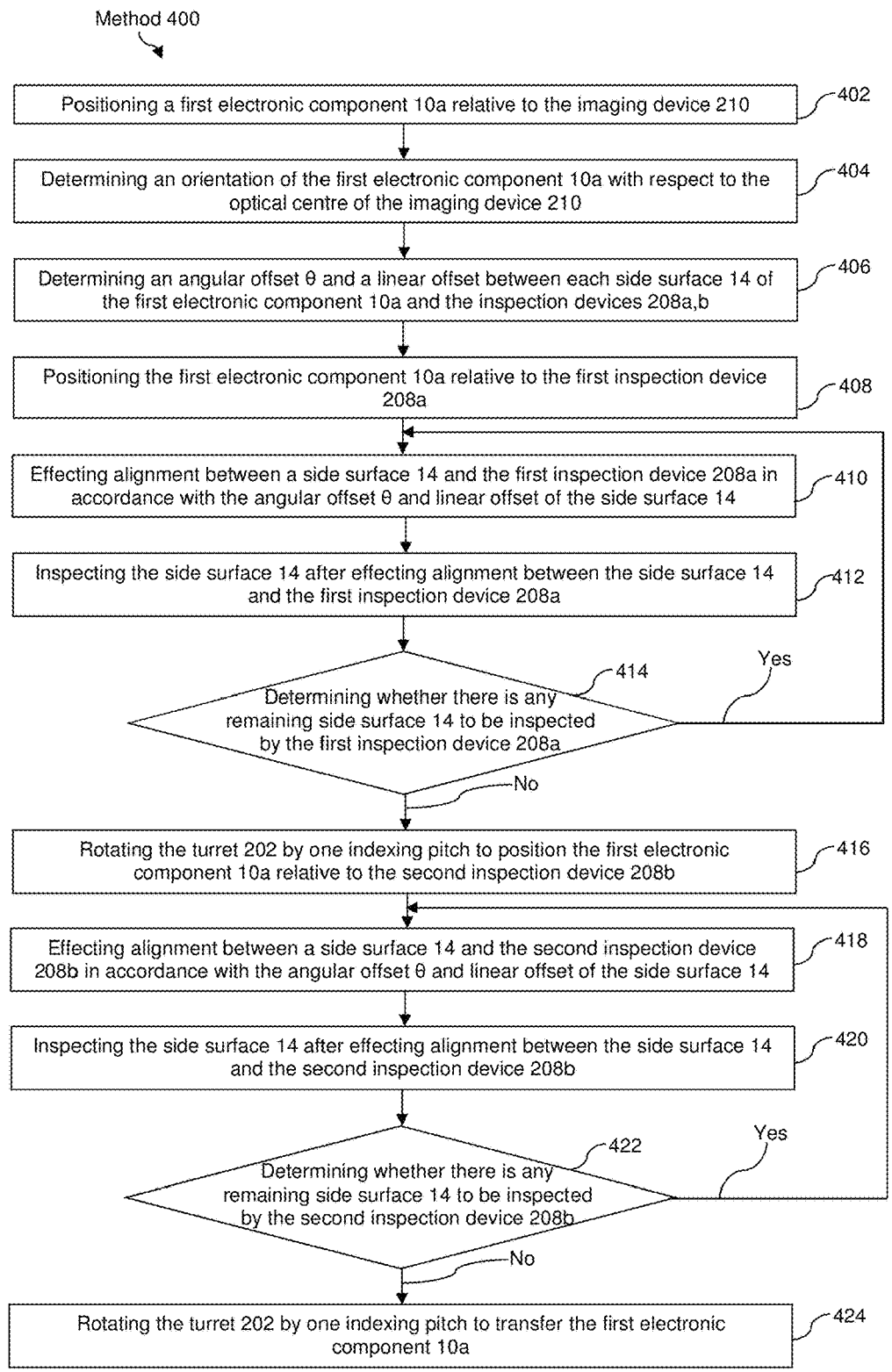
FIG. 13 illustrates a flowchart of a method for aligning and inspecting electronic components, in accordance with the second embodiment of the present disclosure.

In the second embodiment with reference to FIG. 13, there is a method 400 for automated alignment of electronic components 10 with respect to the inspection devices 208a,b for inspecting the electronic components 10. Each electronic component 10 has a plurality of side surfaces 14, such as four side surfaces 14a,b,c,d in a quadrilateral arrangement. Like the method 300, the method 400 may be performed by a computing system, processor, or controller of the apparatus 200. While various steps of the method 400 are described below, for the purpose of brevity, various aspects/details of the method 300 described above apply analogously to the method 400.

The method 400 includes a step 402 of positioning a first electronic component 10a relative to the imaging device 210. Specifically, a first pick head 204a transfers the first electronic component 10a to be positioned above or indexed to the imaging device 210. At the same time, a second electronic component 10b is picked up by a second pick head 204b and the second electronic component 10b is positioned one indexing pitch behind the first electronic component 10a.

The method 400 includes a step 404 of determining, by the imaging device 210, an orientation of the first electronic component 10a with respect to the optical centre of the imaging device 210. As the imaging device 210 is in a fixed position with respect to the inspection stations 206a,b, the positions of the inspection devices 208a,b are known with respect to the optical centre of the imaging device 210 and the circumferential travel path. In a subsequent step 406, the imaging device 210 determines an angular offset θ and a linear offset between each side surface 14a/b/c/d of the first electronic component 10a and the inspection devices 208a, b.

The method 400 includes a step 408 of positioning the first electronic component 10a relative to the first inspection device 208a. At the same time, the second electronic component 10b is positioned relative to the imaging device 210. The imaging device 210 determines an orientation of the second electronic component 10b with respect to the optical centre of the imaging device 210. Specifically, the imaging device 210 determines an angular offset θ and a linear offset between each side surface 14a/b/c/d of the second electronic component 10b and the inspection devices 208a,b.

As the first electronic component 10a is positioned adjacent to the first inspection device 208a, there is a step 410 of effecting alignment between a side surface 14 such as the first side surface 14a and the first inspection device 208a in accordance with the angular offset θ and linear offset of the first side surface 14a. The step 410 may be achieved by performing the steps 310 and/or 312 of the method 300 using adjustment devices. The adjustment devices may include rotary motors 214 coupled to each of the pick heads 204a,b and linear actuators 216 coupled to each of the inspection devices 208a,b.

The first inspection device 208a is configured for inspecting one or more side surfaces 14. In one variant, the first inspection device 208a is configured for inspecting the first side surface 14a and second side surface 14b. The method includes a step 412 of inspecting the first side surface 14a after effecting alignment between the first side surface 14a and the first inspection device 208a.

The method 400 includes a step 414 of determining whether there is any remaining side surface 14 to be inspected by the first inspection device 208a. If yes, the step 414 returns to the step 410. In this subsequent iteration of the step 410, a subsequent side surface such as the second side surface 14b is aligned with the first inspection device 208a in accordance with the angular and linear offsets of the second side surface 14b. Similarly, the subsequent iteration of the step 412 inspects the second side surface 14b after effecting alignment between the second side surface 14b and the first inspection device 208a.

After the step 414 has determined that the first side surface 14a and second side surface 14b have been inspected by the first inspection device 208a, the step 414 proceeds to a step 416 of rotating the turret 202 by one indexing pitch to position the first electronic component 10a relative to the second inspection device 208b. The rotation of the turret 202 also positions the second electronic component 10b relative to the first inspection device 208a.

As the first electronic component 10a is positioned adjacent to the second inspection device 208b, there is a step 418 of effecting alignment between a side surface 14 such as the third side surface 14c and the second inspection device 208b in accordance with the angular and linear offsets of the third side surface 14c. The method includes a step 420 of inspecting the third side surface 14c after effecting alignment between the third side surface 14c and the second inspection device 208b.

The second inspection device 208b is configured for inspecting one or more side surfaces 14. Following the variant described above, the second inspection device 208b is configured for inspecting the third side surface 14c and fourth side surface 14d, as the first side surface 14a and second side surface 14b have already been inspected by the first inspection device 208a. The method 400 includes a step 422 of determining whether there is any remaining side surface 14 to be inspected by the second inspection device 208b. If yes, the step 422 returns to the step 418. In this subsequent iteration of the step 418, a subsequent side surface such as the fourth side surface 14d is aligned with the second inspection device 208b in accordance with the angular and linear offsets of the fourth side surface 14d. Similarly, the subsequent iteration of the step 420 inspects the fourth side surface 14d after effecting alignment between the fourth side surface 14d and the second inspection device 208b.

At the same time during the steps 418 and 420, as the second electronic component 10b is positioned adjacent to the first inspection device 208a, the steps 410, 412, and 414 are iterated for the first side surface 14a and second side surface 14b of the second electronic component 10b. Thus, one of the side surfaces 14a/b of the second electronic component 10b is being aligned and inspected at the same time as one of the side surfaces 14c/d of the first electronic component 10a. More broadly, multiple side surfaces 14 of the electronic components 10a,b are simultaneously inspected by the inspection devices 208a,b.

After the step 422 has determined that the third side surface 14c and fourth side surface 14d have been inspected by the second inspection device 208b, the step 422 proceeds to a step 424 of rotating the turret 202 by one indexing pitch to transfer the first electronic component 10a, such as to a subsequent station for further processing. The rotation of the turret 202 also positions the second electronic component 10b relative to the second inspection device 208b. As the second electronic component 10b is positioned adjacent to the second inspection device 208b, the steps 418, 420, and 422 are iterated for the third side surface 14c and fourth side surface 14d of the second electronic component 10b. It will be appreciated that the method 400 is repeated for subsequent electronic components 10 transferred by the turret 202 to the inspection devices 208a,b.

According to the embodiments described above, one or more inspection devices 208 are configured for sequentially inspecting the side surfaces 14 of an electronic component 10. For example in the first embodiment, individual electronic components 10 are sequentially rotated by the turret 202 to an inspection device 208, and the four side surfaces 14a,b,c,d of each electronic component 10 are sequentially inspected by the inspection device 208. For example in the second embodiment, the first inspection device 208a sequentially inspects the first side surface 14a and second side surface 14b, and subsequently the second inspection device 208b sequentially inspects the third side surface 14c and fourth side surface 14d. Moreover, the one or more inspection devices 208 are configured for simultaneously inspecting multiple side surfaces 14 of a plurality of electronic components 10. For example in the second embodiment, the first inspection device 208a inspects the first side surface 14a of the second electronic component 10b while the second inspection device 208b inspects the third side surface 14c of the first electronic component 10a.

Figure 14:
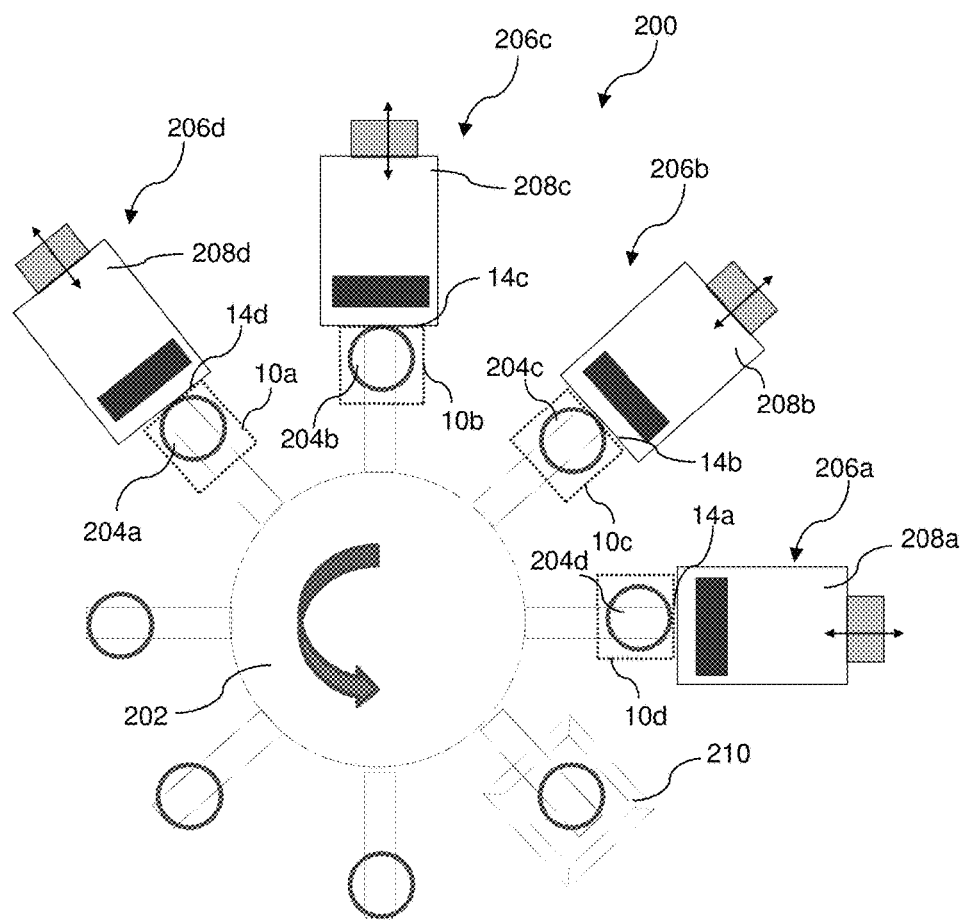
FIG. 14 illustrates an apparatus for aligning and inspecting electronic components, in accordance with a third embodiment of the present disclosure.

In a third embodiment of the present disclosure, there is another variation of the apparatus 200 as shown in FIG. 14. Similar to the first and second embodiments, the apparatus 200 includes a turret 202 for positioning the electronic components 10, a plurality of pick heads 204 for holding the electronic components 10, and an imaging device 210 for determining the angular and linear offsets. However, the apparatus 200 includes a first inspection station 206a, a second inspection station 206b, a third inspection station 206c, and a fourth inspection station 206d. The inspection stations 206a,c,b,d may be positioned one indexing pitch apart from one another. The imaging device 210 may be positioned one indexing pitch before or upstream of the first inspection station 206a and in a fixed position with respect to the inspection stations 206a,b,c,d. Each inspection station 206a/b/c/d has a respective inspection device 208a/b/c/d, and each inspection device 208a/b/c/d is positioned along a circumferential travel path that is concentric to the circumferential travel path of the turret 202.

The inspection devices 208a,b,c,d are arranged such that each inspection device 208a/b/c/d is able to receive an electronic component 10 and all electronic components 10 can be aligned and inspected simultaneously. In one instance as shown in FIG. 14, the fourth inspection device 208d inspects a first electronic component 10a; the third inspection device 208c inspects a second electronic component 10b; the second inspection device 208b inspects a third electronic component 10c; and the first inspection device 208a inspects a fourth electronic component 10d.

Each inspection device 208a/b/c/d is configured for inspecting one side surface 14a/b/c/d of each electronic component 10a/b/c/d. It will be appreciated that the side surfaces 14a/b/c/d are aligned first before inspection. Each pick head 204a/b/c/d holding the respective electronic component 10a/b/c/d may have an angular adjustment device coupled thereto. Each angular adjustment device may be a rotary motor 214 configured for adjusting the electronic component 10a/b/c/d in accordance with the respective angular offsets to align the side surfaces 14a,b,c,d with the inspection devices 208a,b,c,d. Each inspection device 208a/b/c/d may have a linear adjustment device coupled thereto. Each linear adjustment device may be a linear actuator 216 configured for adjusting the inspection device 208a/b/c/d in accordance with the respective linear offsets to focus the inspection device 208a/b/c/d on the side surfaces 14a,b,c,d.

All four side surfaces 14a,b,c,d of the electronic component 10a/b/c/d are inspected by the inspection devices 208a,b,c,d. More specifically, the first inspection device 208a inspects a first side surface 14a; the second inspection device 208b inspects a second side surface 14b; the third inspection device 208c inspects a third side surface 14c; and the fourth inspection device 208d inspects a fourth side surface 14d.

Each electronic component 10a/b/c/d is rotated by the turret 202 to the inspection devices 208a,b,c,d, such that the side surfaces 14a,b,c,d of the electronic component 10a/b/c/d are sequentially inspected by the inspection devices 208a,b,c,d. Furthermore, the electronic components 10a,b,c,d are rotated by the turret 202 to the inspection devices 208a,b,c,d, such that multiple side surfaces 14a,b,c,d of the electronic components 10a,b,c,d are simultaneously inspected by the inspection devices 208a,b,c,d. For example, the fourth side surface 14d of the first electronic component 10a and the first side surface 14a of the fourth electronic component 10d are simultaneously inspected after effecting alignment. This allows the electronic components 10 to be inspected in parallel and at quicker rates, thereby increasing the system throughput or yield of the apparatus 200.

The methods 300 and 400 are thus described above for automated alignment of electronic components 10 with respect to one or more inspection devices 208 for inspecting the electronic components 10. Particularly, the inspection devices 208 inspect the side surfaces 14 of the electronic components 10 after effecting alignment therebetween. This alignment is necessary because the electronic components 10 may be in misaligned orientations when they are picked up by the pick heads 204. The electronic components 10 may also have inconsistent die sizes and cut angles caused during dicing. The alignment allows the inspection devices 208 to precisely focus on the side surfaces 14 to capture focused and clear images of the side surfaces 14 for detection of defects. The alignment is effected prior to inspection by the inspection devices 208, specifically by mechanically adjusting the electronic components 10 and/or inspection devices 208 by adjustment devices including rotary motors 214 and linear actuators 216. More specifically, the electronic components 10 are adjusted by the rotary motors 214 without physically contacting any of the side surfaces 14, thereby avoiding damage to the side surfaces 14. In some embodiments, the alignment is effected after the electronic components 10 are positioned adjacent to the inspection devices 208. However, it will be appreciated that in some other embodiments, the alignment may be effected while the electronic components are being transferred by the turret 202 towards the inspection devices 208. This reduces the overall time required for alignment and the electronic components 10 can be inspected at a quicker rate.

Various embodiments of the present disclosure have been described above based on an apparatus 200 as illustrated in the figures. The methods 300 and 400 are described in relation to the apparatus 200 in the conventional upright orientation. In this upright orientation, the pick heads 204 hold the electronic components 10 beneath and the imaging device 210 is an up-look camera. In some alternative embodiments, the apparatus 200 has an upside-down or inverted orientation wherein the pick heads 204 hold the electronic components 10 on top of the pick heads 204 and the imaging device 210 is a down-look camera. It will be appreciated that aspects of various embodiments described herein, including the methods 300 and 400, apply analogously to the apparatus 200 in the inverted orientation.

In the foregoing detailed description, embodiments of the present disclosure in relation to a method and apparatus for aligning and inspecting electronic components are described with reference to the provided figures. The description of the various embodiments herein is not intended to call out or be limited only to specific or particular representations of the present disclosure, but merely to illustrate non-limiting examples of the present disclosure. The present disclosure serves to address at least one of the mentioned problems and issues associated with the prior art. Although only some embodiments of the present disclosure are disclosed herein, it will be apparent to a person having ordinary skill in the art in view of this disclosure that a variety of changes and/or modifications can be made to the disclosed embodiments without departing from the scope of the present disclosure. Therefore, the scope of the present disclosure as well as the scope of the following claims is not limited to embodiments described herein.

The invention claimed is:

1. A method for automated alignment of electronic components with respect to one or more inspection devices for inspecting the electronic components, each electronic component having a plurality of side surfaces, the method comprising:
    positioning each electronic component relative to an imaging device;
    determining, by the imaging device, an angular offset and a linear offset between each side surface of the electronic component and the one or more inspection devices;

positioning each electronic component relative to the inspection devices;

effecting alignment between each side surface and the one or more inspection devices in accordance with the respective angular and linear offsets; and inspecting each side surface after effecting alignment between the side surface and the inspection devices.

2. The method according to claim 1, wherein the imaging device is in a fixed position with respect to the inspection devices and positioned along a same travel path of a rotary device.

3. The method according to claim 2, wherein each inspection device is positioned along a travel path concentric to the travel path of the rotary device.

4. The method according to claim 1, further comprising adjusting each electronic component in accordance with the respective angular offsets to align the side surfaces with the inspection devices.

5. The method according to claim 4, wherein each electronic component is adjusted without physically contacting any of the side surfaces thereof.

6. The method according to claim 4, further comprising adjusting each inspection device in accordance with the respective linear offsets to align the inspection device with the side surfaces.

7. The method according to claim 1, further comprising adjusting each inspection device in accordance with the respective angular and linear offsets to align the inspection device with the side surfaces of each electronic component.

8. The method according to claim 1, wherein the inspection devices are configured for sequentially inspecting the side surfaces of an electronic component.

9. The method according to claim 1, wherein the inspection devices are configured for simultaneously inspecting multiple side surfaces of a plurality of electronic components.

10. An apparatus for automated alignment and inspection of electronic components, each electronic component having a plurality of side surfaces, the apparatus comprising:

a rotary device for positioning the electronic components;

a plurality of pick heads arranged circumferentially around the rotary device, each pick head being configured for holding an electronic component;

one or more inspection devices for inspecting the side surfaces of the electronic components;

an imaging device configured for determining an angular offset and a linear offset between each side surface and the inspection devices; and one or more adjustment devices for effecting alignment between each side surface and the inspection devices in accordance with the respective angular and linear offsets, wherein the one or more inspection devices is operative to inspect each side surface after the one or more adjustment devices effect alignment between the side surface and the one or more inspection devices.

11. The apparatus according to claim 10, wherein the imaging device is in a fixed position with respect to the inspection devices and positioned along a same travel path of the rotary device.

12. The apparatus according to claim 11, wherein each inspection device is positioned along a travel path concentric to the travel path of the rotary device.

13. The apparatus according to claim 10, wherein the adjustment devices comprise an angular adjustment device coupled to each pick head, the angular adjustment device configured for adjusting the electronic component held at the pick head in accordance with the respective angular offsets to align the side surfaces with the inspection devices.

14. The apparatus according to claim 13, wherein the angular adjustment device is further configured for adjusting the electronic component without physically contacting any of the side surfaces thereof.

15. The apparatus according to claim 10, wherein the adjustment devices comprise an angular adjustment device coupled to each inspection device, the 20 angular adjustment device configured for adjusting the inspection device in accordance with the respective angular offsets to align the inspection device with the side surfaces of each electronic component.

16. The apparatus according to claim 13, wherein the adjustment devices further 25 comprise a linear adjustment device coupled to each inspection device, the linear adjustment device configured for adjusting the inspection device in accordance with the respective linear offsets to align the inspection device with the side surfaces.

17. The apparatus according to claim 10, wherein each electronic component is rotated by the rotary device to the inspection devices, such that the side surfaces of the electronic component are sequentially inspected by the inspection devices.

18. The apparatus according to claim 10, wherein the electronic components are rotated by the rotary device to the inspection devices, such that multiple side surfaces of the electronic components are simultaneously inspected by the inspection devices.

* * * * *